United States Patent [19]
McGuire et al.

[11] Patent Number: 5,505,940
[45] Date of Patent: Apr. 9, 1996

[54] SPRAYABLE GLUTEN-BASED FORMULATION FOR PEST CONTROL

[75] Inventors: Michael McGuire, Metamora; Baruch Shasha, Peoria, both of Ill.

[73] Assignees: The United States of America as represented by the Secretary of Agriculture, Washington, D.C.; Biotechnology Research & Development Corporation, Peoria, Ill.

[21] Appl. No.: 408,138

[22] Filed: Mar. 21, 1995

Related U.S. Application Data

[63] Continuation of Ser. No. 134,999, Oct. 11, 1993, abandoned.

[51] Int. Cl.$^6$ .......................... A01N 25/00; A01N 25/24; C12N 1/00
[52] U.S. Cl. .................... 424/93.1; 424/195.1; 424/405; 424/407
[58] Field of Search ............................... 424/195.1, 405, 424/407, 93.1

[56] References Cited

U.S. PATENT DOCUMENTS

| | | | |
|---|---|---|---|
| 3,111,416 | 11/1963 | Gaver et al. | 106/146 |
| 3,607,370 | 9/1971 | Aranyi et al. | 117/122 P |
| 3,891,756 | 6/1975 | Kasugai et al. | 424/177 |
| 4,230,687 | 10/1980 | Sair et al. | 424/22 |
| 4,841,669 | 6/1989 | Demarest et al. | 43/131 |
| 5,012,004 | 4/1991 | Takahashi et al. | 568/53 |
| 5,055,491 | 10/1991 | Yano et al. | 514/531 |
| 5,057,141 | 10/1991 | Rodriguez-Kabana et al. | 71/28 |
| 5,074,902 | 12/1991 | Connick, Jr. et al. | 71/79 |
| 5,091,183 | 2/1992 | Yano et al. | 424/405 |
| 5,135,744 | 8/1992 | Alexander et al. | 424/78.17 |
| 5,283,060 | 2/1994 | Shieh | 424/93 L |
| 5,290,749 | 3/1994 | Christians et al. | 504/189 |
| 5,290,757 | 3/1994 | Christians et al. | 504/335 |
| 5,358,863 | 10/1994 | Quimby, Jr. et al. | 435/178 |

FOREIGN PATENT DOCUMENTS 0301278  2/1989  European Pat. Off. .

OTHER PUBLICATIONS

*The Merck Index*, 11th Ed., Merck & Co., Inc. Rahway, N.J., 1989, p. 703.
Chung, O. K., *Cereal Foods World*, 31:242–256 (1986).
Dunkle, R. L., and Shasha, B. S., *Environ. Entomol.* 17:120–126 (1988).
Hughes, P. R., and Wood, H. A., *J. Invertebr. Pathol.* 37:154–159 (1981).
Koestler, R. C., Microencapsulation by interfacial polymerization techniques–agricultural applications, pp. 117–132. In A. F. Kydonieus [ed.] Controlled release technologies: methods, theory, and applications. CRC Press, Boca Raton (1981).
Krull, L. H. and Inglett, G. E., *Cereal Science Today*, 16:232–236, 261 (1971).
Krull, L. H. and Wall, J. S., *Canadian J. of Biochemistry*, 47:581–585 (1969).
Lampman, R. L. and Metcalf, R. L., *Environ. Entomol.* 17:644–648 (1988).
Lance, D. R., *J. Chem. Ecol.* 14:1177–1185 (1988).
Lance, D. R., and Sutter, G. R., *J. Econ. Entomol.* 83:1085–1090 (1990).
Magnuson, K. M., *Cereal Foods World*, 30:179–181 (1985).
McGuire et al., *J. Econ. Entomol.* 84:1652–1656 (1991).
McGuire M. R. and Shasha, B. S., *J. of Econ. Entomol.* 83:1813–1817 (1990).
Meinke et al. *J. Econ. Entomol.* 82:1830–1835 (1989).
Raun et al., *J. of Econ. Entomol.* 59:620–622 (1966).
Shasha et al., *J. Appl. Polym. Sci.* 29:67–73 (1984).
Shasha, B. S. & M. R. McGuire. Starch materials for slow release of pesticides. In D. G. Chasin & L. E. Bode, (eds), Pesticide formulations and application systems. American Society for Testing and Materials, Philadelphia (1991) pp. 33–40.
Shaw et al., *J. Econ. Entomol.* 77:1495–1499 (1984).
Trimnell, D. and Shasha, B. S., *J. Controlled Release* 7:263–268 (1988).
Synek, J., Formulation, development, and application of an insecticide granule, pp. 123–131. In T. M. Kaneko & N. B. Akesson [eds.] Pesticide formulations and application systems: third symposium, ASTM STP 828. American Society for Testing and Materials, Philadelphia, 1983.
Vander Hooven, D. I. B., Corncob granules and pelleted carriers—new, controlled, safer methods of handling pesticides, pp. 132–140. In T. M. Kaneko & N. B. Akesson [eds] Pesticide formulations and application systems: third symposium, ASTM STP 828. American Society for Testing and Materials, Philadelphia, 1983.
Wall et al., *J. Polymer Sci.*, 24:147–161 (1968).
Wall, J. S. and Beckwith, A. C., *Cereal Science Today*, 14:2455–2459 (1969).
Wall, J. S. and Huebner, F. R., *Protein Functionality in Foods* 147:111–130 (1980).
Weissling, T. J. & Meinke, L. J., *J. Econ Entomol.* 84:601–609 (1991).
Wing, R. E. and Otey, T. H., *J. Polym. Sci. Polym. Chem. Ed.* 21:121–140 (1983).
Trimmell et al., "Pesticide Encapsulation Using a Starch–Borate Complex as Wall Material," *J. of Applied Polymer Science*, 27:3919–3928 (1982).
Huebner et al., "Fractionation and Quantitative Differences of Glutenin from Wheat Varieties Varying in Baking Quality," *Cereal Chemistry*, 53(2):258–269 (1976).

*Primary Examiner*—Michael G. Wityshyn
*Assistant Examiner*—Kristin K. Larson
*Attorney, Agent, or Firm*—Arnold, White & Durkee

[57] ABSTRACT

The present invention provides a process of formulating a pest control agent into a sprayable gluten-based formulation. A gluten-based formulation for use in pest control is also provided. The present invention also provides a process of decreasing the population of a pest of a living organism comprising formulating a pest control agent into a sprayable gluten-based formulation and delivering the formulation to the external surface of the living organism.

11 Claims, No Drawings

SPRAYABLE GLUTEN-BASED FORMULATION FOR PEST CONTROL

This application is a continuation of application Ser. No. 08/134,999, filed Oct. 11, 1993, now abandoned

TECHNICAL FIELD OF THE INVENTION

The present invention relates to a sprayable gluten-based formulation, a process of incorporating a biological or chemical substance such as a pest control agent into such a formulation and the use of such a formulation to decrease the population of a pest of a living organism.

BACKGROUND OF THE INVENTION

Myriad approaches have been pursued to control pests. Many of these methods and compositions are directed to the control of pests that attack plants, most notably commercially valuable plants. Although much current agricultural research has pest control as its objective, pest destruction of plants and plant products is still a major problem.

Control of pests of plants, livestock, and households has been accomplished with the aid of chemical and biological control agents. Unfortunately, approaches using these agents may fail due to inadequate formulation of the pesticides. In particular, many formulations are adversely affected by major environmental hindrances. By way of example, rainfall can wash away control agent deposits and sunlight can inactivate the active agent.

Starch and flour have been studied extensively (McGuire and Shasha, 1990; U.S. patent applications Ser. Nos. 07/730,763 and 07/913,565, the disclosures of which are incorporated herein by reference) as materials to encapsulate pesticides. Most of this work has been done with granular matrices in efforts to reduce the amount of chemical pesticide needed to control pests or to protect environmentally sensitive pesticides (usually biological control agents) and thus extend their activity. While efforts with these granular formulations have been successful, by far, the majority of pesticides are applied as sprayable formulations. Shasha and McGuire disclose such a sprayable formulation for microbial insecticides consisting of a mixture of cornstarch or flour and sucrose. This formulation enhances and extends the performance of the active agents (U.S. pat. No. 5,061,697). Formulations of this type are essential for the widespread use of biological control agents and for enabling the reduction of potentially environmentally hazardous chemical pesticides. Formulations that are effective with lower active ingredient rates are possible through the judicious use of protectants, attractants, or other additives that synergize ingredient activity.

However, these formulations require additives at solids rates of 2 to 6% of the spray volume. These formulations, therefore are most useful under low spray volume conditions.

The present invention utilizes a product other than starch to produce a film upon spraying and is distinct from previous technology. While other products from farm commodities have been used as carriers in granular formulations, little work has yet been done with these products for sprayable formulations. For example, wheat gluten has extensively been used in the baking industry but has never before been tested as a pesticide formulation ingredient. Our tests with gluten-based formulations suggest a significant improvement over existing technology because solids rates of a maximum of 1% show improved rainfastness and survival of the active agent. These types of solids rates should extend the usefulness of the formulation to a wider range of spray systems.

BRIEF SUMMARY OF THE INVENTION

The present invention provides, in one aspect, a process of preparing a sprayable gluten-based formulation incorporating a pest control agent comprising admixing an effective amount of a gluten, a pesticidally effective amount of the pest control agent, and water.

The formulation has a non-neutral pH value. In a preferred embodiment, the pH value of the formulation is less than about 5.5 or greater than about 9.5. More preferably, the formulation has a pH value of from about 3.0 to about 5.0 or from about 10.0 to about 12.0.

In a preferred embodiment, the formulation, including the pest control agent, adheres to a plant surface and, more preferably to a plant foliar stirface. In another preferred embodiment, the formulation adheres to an external surface of an animal, preferably skin, fur or hair.

In another aspect, the present invention contemplates a process of decreasing the population of a pest of a living organism comprising delivering to an external stirface of the living organism a sprayable gluten-based formulation that (a) incorporates a pest control agent and (b) adheres to that surface. Where the living organism is a plant, the external surface is preferably a foliar stirface. Where the living organism is an animal, the external stirface is preferably skin, hair or fur. A formulation used in that process is preferably prepared in accordance with a process of the present invention.

The present invention, thus, contemplates a process of decreasing the population of a pest of a living organism comprising the steps of:

(a) formulating the pest control agent into a sprayable gluten-based formulation by (i) admixing a pesticidally effective amount of the pest control agent, an effective formulating amount of gluten and water; and (b) delivering the formulation to the external surface of the living organism.

The gluten and pest control agent used in a process of decreasing the population of a pest of a living organism are the same as set forth above.

In yet another aspect, the present invention contemplates a sprayable gluten-based formulation that incorporates a pest control agent. Preferably, the formulation is made by a process of the present invention.

The methods and compositions of the present invention solve a significant number of the problems in the previous methods of pest control. A formulation of the present invention adheres to an external surface of a living organism despite exposure of those organisms to environmental forces which dislodge other types of formulations or granules.

DETAILED DESCRIPTION OF THE INVENTION

The present invention provides a process of formulating a chemical or biological material and, in particular a pest control agent, in a sprayable glutenbased formulation and to the composition of such a formulation. The present invention also provides a process of decreasing the population of a pest of a living organism. A formulation of the present invention comprises gluten, a biological or chemical substance such as a pest control agent and an aqueous solvent.

This invention relates to sprayable formulations of chemical and microbial pesticides that are effective in low amounts and resist wash-off from rainfall. Solubilized gluten, specifically wheat gluten, is used to disperse the pesticide and entrap it on leaf or other surfaces. The pesticide then remains viable under harsh environmental conditions. Gluten and specifically wheat gluten compositions are disclosed for the delivery of biological or chemical pest control agents. Due to the low solubility of wheat gluten in water at a neutral pH, a pH adjuster such as citric acid or acetic acid is included to obtain an acidic pH. Alternatively, an alkali component such as ammonium hydroxide, trisodium phosphate or potassium hydroxide is added to obtain an alkaline pH. The pH adjuster can be either dissolved in water prior to the addition of gluten-active ingredient or can be included with the gluten-active ingredient.

I. Process of Preparing a Sprayable Formulation

In one aspect, the present invention provides a process of formulating a pest control agent in a sprayable gluten-based aqueous formulation. Such a formulation process comprises admixing an effective formulating amount of a gluten, a pesticidally effective amount of the pest control agent and an aqueous solvent having a non-neutral pH that allows for solubilization of the gluten.

Where applied to a living organism, the formulation, including the pest control agent, adheres to an external surface of that organism. As used herein, the term "adhere" or any of its grammatical equivalents means that the formulation sticks to a target surface on which the formulation is applied. Exemplary surfaces to which a formulation of the present invention adheres include an external stirface of a living organism and artificial surfaces such as those made of glass, metal, plastic, wood, and the like. In a preferred embodiment, a formulation of the present invention adheres to an external surface of a living organism such as a plant or animal. Where the living organism is a plant, a preferred external stirface is a foliar surface. Where the living organism is an animal, a preferred external surface is skin, fur or hair.

As used herein, the term "gluten" refers to a water insoluble protein found in cereal grains. Gluten is primarily comprised of gliadin, glutenin, globulin and albumin. Wheat gluten is insoluble in aqueous solutions at neutral pH, but readily soluble in non-neutral aqueous solutions. Wheat gluten comprises about 80–90% of the proteins found in wheat (Krull et al., 1971).

Gluten can be obtained commercially or can be prepared from cereal grains such as wheat. By way of example, wheat gluten can be prepared by mixing wheat flour with an appropriate amount of water to form a dough and then washing out the starch from that dough in a stream of water. Gluten can be commercially prepared in accordance with such a process using either 1) a "dough" or "Martin" process, or 2) "slurry" or "Raisio" process. Gluten, prepared in accordance with any one of the above processes is obtained in a wet from Dry or "vital" gluten can be obtained from wet gluten by drying.

Gluten has a variety of uses in the food industry. Exemplary uses include baking, milling and in manufacturing pet foods, breakfast cereals, meat, seafood analogs, pasta, cheese analogs, aqua culture feed and snacks Because of its adhesive, thermo-setting, and film-forming properties, gluten has recently been used in a variety of non-food uses (Krull et al., 1971). Exemplary such non-food uses include the manufacture of biodegradable surfactants, the manufacture of paper coatings and wallpaper adhesives and the production of pressure-sensitive adhesive tapes (Krull et al., 1971; Magnuson, 1985). The present invention describes for the first time, a use of gluten in the preparation of sprayable formulations for use in pest control.

As used herein, a "pest control agent" indicates a substance that serves to repel a pest from a living organism, decrease or inhibit the growth, development or destructive activity of a pest. A pest can be a plant, an animal or a microorganism. Exemplary pests include insects, spiders, nematodes, fungi, weeds, bacteria and other microorganisms. Thus, a pest control agent can be insecticide, a pesticide, a fungicide, a herbicide, antibiotic, an anti-microbial, and the like. A pest control agent can also be a mixture of two or more agents.

Exemplary pest control agents are dimilin (N-{[(4-chlorophenyl) amino] carbonyl}-2,6-difluorobenzamide), malathion [(dimethoxyphosphinothioyl)thio]butanedioic acid diethyl ester), carbaryl (1-naphthalenol methylcarbamate) and diazinon (0,0-diethyl 0-[6-methyl-2-(1-methylethyl)- 4-pyrimidinyl]phosphorothioate); 2,4-D (2,4-dichlorophenoxyacetate sodium salt), a 2,4-D ester (2,4-dichlorophenoxyacetate isopropyl ester); metolachlor (2-Chloro-N-(2-ethyl-6-methylphenyl)-N-(2-methoxy-1-benzenedicarboxylate); glyphosate (N-(phosphonomethyl) glycine); paraquat (1, 1'-dimethyl-4, 4'-bipyridinium salt); and trifiuralin (1, 1, 1-trifluoro- 2, b-dinitro-N, N-dipropyl-p-toluidine). Pesticides, insecticides, herbicides, fungicides, antimicrobials and antibiotics are commercially available. An exemplary list of such substances can be found in U.S. Pat. No. 4,911,952, the disclosure of which is incorporated herein by reference.

A pest control agent can be a biological or chemical material. As used herein, the phrase "biological material" means a living organism or a substance isolated, produced or otherwise derived from a living organism (e.g., a toxin or a hormone). Thus, a biological pest control agent can be an inanimate form of a once living organism. The use of such a biological pest control agent is exemplified hereinafter in Examples 1–3 and 6–9.

Exemplary biological pest control agents include a bacteria such as the bacterium *B. thuringiensis*, Baculoviridae, e.g., *Autographa californica*. nuclear polyhedrosis virus, protozoa such as Nosema spp., fungi such as Beauveria spp., and nematodes.

As used herein, the phrase "chemical material" means a synthetically prepared compound or composition. Exemplary chemical pest control agents include thiocarbonates, dinitroanilines, organophosphates, and alachlor.

As used herein, the phrase "effective amount" means that amount of a pest control agent sufficient to bring about the desired response (e.g., repel or kill a pest). "A pesticidally effective amount" is that amount which, when delivered to an external surface of a living organism, results in a significant mortality rate of a pest when compared to the mortality rate of that same pest exposed to a living organism not treated with that agent.

A pest control agent can further comprise an additive or adjunct such as a dispersant, a phagostimulant (a feeding stimulant), an attractant, an ultraviolet light protectant, a preservative and an inert filler. Examples of such additives can be found in U.S. Pat. No. 4,911,952, the disclosure of which is incorporated herein by reference.

In a preferred embodiment, the additive is an attractant or a phagostimulant. An attractant is preferably an aqueous, non-soluble, or hydrophobic substance that attracts a pest to the spray deposit. A phagostimulant is a substance that stimulates ingestion of the spray deposit.

A preferred attractant is a pheromnone or a volatile feeding attractant such as p-methoxycinnamaldehyde. An exemplary and preferred phagostimulant is cucurbitacin obtained from powdered, dried root of the buffalo gourd, or Xoax®, a feeding stimulant containing cotton seed flour, sugar, vegetable lipid oil and ethoxylated ester (CCT Corporation, Litchfield Park, Ariz.). Exemplary sugars are mono-, oligo- and polysaccharides containing from about 1 to about 50 saccharide units. In a preferred embodiment, a sugar is a disaccharide such as sucrose, or a molasses.

Exemplary ibrmulations comprising one or more of the above ingredients are described in detail hereinafter in Examples 1 through 12.

Admixing is carried out at a temperature of froin about 5° C. to about 100° C. and, preferably, at a temperature of from about 10° C. to about 25° C. The gluten, pest control agent, and water can be admixed in any order.

Typically, the concentration of gluten in a formulation of the present invention is froin about 0.1 percent by weight (grams/100 ml) to about 5 percent by weight. More preferably, the concentration of gluten is from 0.25 percent by weight to about 1.5 percent by weight. The only limitation on the concentration of gluten is the solubility of gluten. Solubility is enhanced at non-neutral. pH values.

The pH value of a formulation of the present invention is adjusted with an alkalinizing or an acidifying agent. Any alkalinizing or acidifying agent can be used to adjust formulation pH so long as that agent does not adversely affect the formulation or the biological or chemical substance contained therein. In a preferred embodiment, an acidifying agent is an organic acid. A preferred organic acid is citric acid. The amount of an acidifying agent used depends, as is well known in the art, upon the strength of that acidifying agent and the desired pH.

The formulation has a non-neutral pH value. In a preferred embodiment, the pH value of formulation is less than about 5.5 or greater than about 9.5. More preferably, the formulation has a pH value of from about 3.0 to about 5.0 or from about 10.0 to about 12.0.

A preferred alkalinizing agent is a basic salt. More preferably, an alkalinizing agent is a metal hydroxide such as NaOH or KOH. The amount of an alkalinizing agent used depends, as is well known in the art, upon the dissociation constant of that agent and the desired pH.

A formulation of the present invention can also comprise a buffer to maintain the pH at a predetermined value. Any buffer can be used so long as that buffer does not adversely affect the formulation or the pest control agent contained therein. A buffer can also be used as the acidifying or alkalinizing agent. Thus, in one embodiment, formulation pH can be set and maintained with a form of buffer pairs such as phosphoric acid-phosphate, citric acid-citrate and acetic acid-acetate.

A formulation of the present invention can also be prepared to comprise water-dispersible granules. In accordance with such an embodiment, a formulation comprises, in addition to a pest control agent, 1) an agglomerating agent that promotes formation of granules that contain gluten, 2) a dispersing agent that promotes separation of gluten particles upon contact with the aqueous solvent, or 3) both an agglomerating and a dispersing agent. In a preferred embodiment, a dispersing or agglomerating agent is premixed with gluten prior to the addition of the aqueous solvent. A preferred dispensing agent or an agglomerating agent is a vegetable oil such as corn oil or soybean oil. A preferred agglomerating agent is molasses. A description of a formulation made by precoating gluten with corn oil can be found hereinafter in Example 3.

II. Process of Pest Control

In another aspect, the present invention contemplates a process of decreasing the population of a pest of a living organism, which process comprises the steps of:

(a) formulating a pest control agent into a sprayable gluten-based aqueous formulation in accordance with a process of the present invention; and (b) delivering a pesticidally effective amount of the formulation to an external surface of the organism.

A pest control agent that can be used with this process is the same as set forth above in relation to a process of preparing a sprayable formulation. The selection of a pest control agent depends upon the pest to be controlled as well as the nature of the living organism to be protected.

Preferably, the pest control agent comprises at least one of *Bacillus thuringiensis*, entomopoxvirus, a chemical insecticide, and a pest attractant. In a more preferred embodiment, a pest control agent comprises a pesticide and an attractant, the purpose of which is to lure a pest to the formulation containing the pest control agent. The attractant can be volatile such as a pheromone.

A pesticidally effective amount of a pest control agent in a formulation is delivered to a living organism. Means for determining a pesticidally effective amount for a given pest control agent are well known in the art. In a preferred embodiment, a formulation is sprayed onto an external surface of the living organism. By way of example, formulations are applied to plants using a Derives Research Track Sprayer Booth. The spray is calibrated to deliver formulation at a rate equalling 25 gal/A at 59 PSI with a single 8002 flat fan nozzle.

Use of a formulation of the present invention has the advantage of decreasing the amount of pest control agent needed to protect a given area of surface area by minimizing loss of delivered pest control agents due to environmental conditions. Environmental disturbances include wind, rain and snow. A major problem in the use of pest control agents is the loss of such agents from target organisms. In the present invention, a formulation is produced which, upon spraying on a surface, permits agents in that formulation to adhere to that surface even in the presence of additional water. The use of a formulation of the present invention thus allows for earlier application of a pest control agent and extends the "window" of application necessary for the economic control of a pest that can enter an area over an extended period of time. Still further, a process of the present invention increases the effectiveness of a pest control agent. Because a control agent adheres to surfaces for an extended period of time, the contact between the pest control agent and the target organism to which it is applied is substantially prolonged.

III. Sprayable Gluten-Based Formulation

In a still further aspect, the present invention contemplates a sprayable gluten-based formulation that incorporates a biological or chemical substance and, preferably a pest control agent. As used herein, the term "gluten-based" indicates that a formulation of the present invention comprises gluten.

A sprayable-gluten based formulation of the present invention comprises an effective formulating amount of gluten, a pesticidally effective amount of a pest control agent and an aqueous solvent. Typically, the concentration of gluten in a formulation of the present invention is from about 0.1 grams/100 ml to about 5 grams/100 ml. Even more preferably, the concentration of gluten is from about 0.25 grams/100 ml to about 1.5 grams/100 ml. A gluten-based formulation of the present invention has a non-neutral pH value and preferably has a pH value of from about 3.0 to about 5.0 or from about 10.0 to about 12.0. A preferred aqueous solvent is water. As set forth above, a formulation of the present invention can further comprise acidifying or alkalinizing agents, a buffer and an additive such as a pest attractant or a phago stimulant. A formulation of the present invention is preferably made by a process as set forth above.

Upon application of a formulation of the present invention to a surface, a pest control agent in the formulation adheres to a variety of surfaces including but not limited to glass, metal, plastic, wood, and to an external surface of a living organism such as an animal or plant. In a preferred embodiment, an external surface is an external surface of a plant or animal. Exemplary and preferred surfaces are a plant foliar surface, animal skin, fur and hair. In a preferred embodiment, a formulation of the present invention is made by a process of this invention.

The following examples have been included to illustrate preferred modes of the invention. Certain aspects of the following examples are described in terms of techniques and procedures found or contemplated by the present inventors to work well in the practice of the invention. These examples are exemplified through the use of standard laboratory practices. In light of the present disclosure and the general level of skill in the art, those of skill will appreciate that the following examples are intended to be exemplary only and that numerous changes, modifications and alterations can be employed without departing from the spirit and scope of the invention.

EXAMPLES

All new formulations containing technical grade *B. thuringiensis* (Bt), supplied by Abbott Laboratories as a bioassayed preparation containing 70,000 International Units/rag were compared against a commercial formulation of Bt, (Dipel 2X), containing 32,000 international units (Iu)/mg. Tests were conducted, either under dry and/or wet conditions. Under wet conditions, after application of formulations, each treatment received 2 inches of simulated rain in a spray chamber. For bioassays, unless otherwise stated, cotton was used as the test plant and European corn borer larvae were used as the test insect.

General Testing Procedure

A. Application of formulations. Formulations were applied to whole cotton plants using a Derives Research Track Sprayer Booth. The spray is calibrated to deliver formulation at a rate equalling 25 gal/A at 59 PSI with a single 8002 flat fan nozzle.

B. Simulated rainfall. After allowing the plants to dry, half were subjected to simulated rain/all in the sprayer booth. Approximately 2 inches (as measured by a rain gauge) rain was allowed to fall over a 1.45 hr period through a FL5VC Full cone nozzle at 32 PSI. Continuous movement of the nozzle, back and forth, allowed for an even dispersion of water throughout the chamber and over the leaves.

C. After the plants dried, leaf disks (33 cm$^2$) were cut from the treated plants and inverted in a 9 cm diameter plastic petri dish lined with white filter paper. Ten European corn borer neonate larvae (*Ostrinia nubilalis*) (ECB) were added to each dish and then each dish was twice wrapped with parafilm to seal the edges. After 3 days in the dark at 27° C., dishes were opened and percent mortality obtained. In general, 10 leaf disks were tested for each treatment.

EXAMPLE 1

500 milliliters (ml) of a 0.011% (w/v) solution of sodium hydroxide and 0.15% (w/v) urea were mixed in a blender with *B. thuringiensis* tech powder (50 mg). Formulations were made without gluten or with either 5 grams (1%) or 2.5 grams (0.5%) of gluten. The pH of the formulations was about 10.6.

| | % ECB Mortality | |
|---|---|---|
| | Rain | No Rain |
| Untreated control | — | 0 |
| Gluten 1% - NaOH-urea control | — | 12 |
| NaOH-urea - Bt tech | 15 | 75 |
| Gluten 0.5%-NaOH-urea-Bt tech | 24 | 94 |
| Gluten 1%-NaOH-urea-Bt tech | 71 | 94 |
| Dipel 2x | 8 | 87 |

EXAMPLE 2

The following gluten formulations were made:

A. Dipel 2X (88 mg) was dispersed in 200 ml of a 0.1% (w/v) molasses solution in deionized water.

B. *B. thuringiensis* technical powder (40 mg) was dry mixed with gluten (2 g) and mixed in a Waring blender with 200 ml of an aqueous solution comprising deionized water, 0.1% (w/v) molasses and 0.1% (w/v) citric acid to yield a formulation with a pH of about 3.5.

C. *B. thuringiensis* technical powder (40 mg) was dry mixed with gluten (2 g) and mixed in a Waring blender with 200 ml of an aqueous solution comprising deionized water, 0.1% (w/v) molasses and 0.05% (w/v) KOH.

D. *B. thuringiensis* technical powder (40 mg) was dry mixed with gluten which was precoated with corn oil in a ratio of 10:1 (w/w) and mixed in a Waring blender with 200 ml of an aqueous solution comprising deionized water, 0.1% (w/v) molasses and 0.1% (w/v) citric acid to yield a formulation with a pH of about 3.5.

E. *B. thuringiensis* technical powder (40 mg) was dry mixed with gluten which was precoated with corn oil in a ratio of 10:1 (w/w) and mixed in a Waring blender with 200 ml of an aqueous solution comprising deionized water, 0.1% (w/v) molasses and 0.05% (w/v) KOH.

F. Calcium chloride dihydrate (2 g) was dissolved in molasses (20 g) to form a molasses solution. Gluten (10 g) was dispersed with that molasses solution (2 g) to form dispersible granules. A sample of the gluten-molasses dispersible granules (2 g) was n-fixed with 200 ml of a 0.1% (w/v) citric acid solution and 40 mg. Bt tech as in (B). The results of studies using the above/formulations are summarized below.

| | % ECB Mortality | |
|---|---|---|
| Formulation | Rain | No Rain |
| Untreated control | — | 3.9 |
| A | 28.1 | — |
| B | 57.1 | 92.6 |
| C | 81 | 98.6 |
| D | 66 | 68.2 |
| E | 75.5 | 98.8 |
| F | 62.7 | 92.6 |

EXAMPLE 3

The following formulations were prepared.

A. Molasses control, 0.2% (w/v) molasses in deionized water.

B. Dipel 2X control, 22 mg active ingredient in deionized water (50 ml).

Dipel. 2X, (22 mg) in 0.2% (w/v) molasses in deionized water (50 ml).

D. Bt tech (10 mg) was added to a 0.1% (w/v) citric acid—aleionized water solution (50 ml). 0.5 g gluten was added to the solution.

E. Bt tech (10 mg) was added to a 0.1% (w/v) citric acid—0.2% (w/v) molasses—aleionized water (50 ml) solution. 0.5 g gluten was added to the solution.

F. Bt tech (10 mg) was added to a 0.025% (w/v) KOH—deionized water (50 ml) solution. 0.5 g gluten was added to the solution.

G. Bt tech (10 mg) was added to 0.025% (w/v) KOH—0.2% (w/v) molasses—deionized water solution. 0.5 g gluten was added to the solution. The results from studies using the above formulations are summarized below.

| Formulation | % ECB Mortality | |
|---|---|---|
| | Rain | No Rain |
| Untreated control | — | 14.5 |
| A | — | 8 |
| B | 28.4 | 89.2 |
| C | 32.3 | 99 |
| D | 61 | 59.4 |
| E | 73.2 | 96.2 |
| F | 77.2 | 98.2 |
| G | 62.2 | 100 |

EXAMPLE 4

Gluten and acid can be added together or separately. Wheat gluten (20 g) was dry mixed with powdered citric acid hydrate (2 g) and then added to deionized water (2 liters) in a blender. This yielded a mixture of solubilized gluten containing 1.1% (w/v) solid with a pH of 3.54.

EXAMPLE 5

Gluten and alkali can also be added together before addition to water. Wheat gluten (20 g) was dry mixed with powdered potassium hydroxide (2 g) and then added to deionized water (2 liters) in a blender. This yielded a mixture of solubilized gluten containing 1.1% (w/v) solid with a pH of 11.78. When the experiment was repeated using tap water instead of deionized water, the pH was 11.17.

Wheat gluten (60 g) was dry mixed with powdered potassium hydroxide (3 g) and then added to deionized water (2 liters) in a blender. This yielded a mixture of solubilized gluten with a pH of 11.78, which after dilution with deionized water (4 liters) had a pH of 11.35.

EXAMPLE 6

The performance of Bt tech versus Dipel 2X in the presence or absence of gluten was compared. The dose of Bt tech used was 10 mg/50 ml deionized water or the equivalent amount of Dipel 2X (22mg/50 ml deionized water). The gluten concentration was 1% and the concentration of $Na_3PO_4$ (TSP) was 0.1% (w/v).

| | % ECB Mortality | |
|---|---|---|
| | Rain | No Rain |
| Untreated control | — | 12.8 |
| Gluten TSP + Dipel 2X | 46.5 | 100 |
| Gluten TSP + Bt tech | 87.2 | 97.2 |
| Dipel 2X + TSP | 19.0 | 95 |
| Tech Bt + TSP | 13 | 99 |
| Dipel 2X | 15.5 | 97 |
| Bt tech | 13.7 | 94.5 |

EXAMPLE 7

The efficacy of Bt tech treatment was compared with 20 mg Dipel 2X/50 ml deionized water, using several gluten concentrations and in the presence of $Na_3PO_4$ (TSP). The $Na_3PO_4$ concentration was 0.05% (w/v) and had a pH of 9.4.

| | % Mortality | |
|---|---|---|
| | Rain | No Rain |
| Dipel 2X in Water | 8 | 78 |
| Dipel 2X + TSP | 44 | 85 |
| Gluten 0.25% + TSP + Dipel 2X | 41 | 80 |
| Gluten 0.50% + TSP + Dipel 2X | 54 | 87 |
| Gluten 1.0% + TSP + Dipel 2X | 65 | 80 |

EXAMPLE 8

Deionized water (180 ml) was mixed in a blender with an ammonium hydroxide solution (5 ml) to yield a solution of pH 11.0. Wheat gluten (20 g) and 40 mg Bt tech powder (70,000 I.U./mg) were added and the formulation was sprayed on cabbage leaves to control cabbage looper (*Trichoplusia ni* [*T. ni*]). Results were compared against Bt tech in the absence of gluten and against Dipel 2X. Larval mortality after 6 days expostire on cabbage plants is summarized below.

| | % T. ni Mortality |
|---|---|
| Control - Water | 18 |
| Control - Bt tech | 43 |
| Control Dipel 2X | 65 |
| Gluten Bt tech | 84 |

EXAMPLE 9

The efficacy of Bt in a gluten formulation was tested in field trials against *Trichoplusia ni* (Hubner). Formulations were applied to cabbage leaves under rain and no rain conditions. The leaves were examined after 0, 2, 4 and 7 days and results are expressed in percentage mortality of *Trichoplusia ni*. Rain was simulated using evenly spaced Rainbird brand impact-style lawn sprinklers. Water was delivered at approximately 0.5 inches per hour over the canopy. Approximately 2 inches rain was applied. Plants not receiving rain were covered with plastic tents. The formulations tested were:

A) Water only

B) 0.1% (w/v) molasses control

C) Dipel 2X (4 g/L)

D) Dipel 2X (4 g/L) in 0.1% (w/v) molasses

E) Bt tech (1.83 g/L)+ gluten (1%) (w/v)+citric acid (CA) (0.1%) (w/v)

F) Bt tech (1.83 g/L)+gluten (1%) (w/v)+citric acid (CA) (0.1%) (w/v)+molasses (w/v)

G) Bt tech (1.83 g/L)+gluten (1%) (w/v)+KOH (0.025%) (w/v)

H) Bt tech (1.83 g/L)+gluten (1%) (w/v)+KOH (0.025%) (w/v)+mol (0.1% ) (w/v)

| | Days after Treatment | | | | | | | |
|---|---|---|---|---|---|---|---|---|
| Formulation | 0 No Rain | 0 Rain | 2 No Rain | 2 Rain | 4 No Rain | 4 Rain | 7 No Rain | 7 Rain |
| A | 23.8 | 14.7 | 14.9 | 7.4 | 17.8 | 14.8 | 11.2 | 44.4 |
| B | 12.3 | 13.0 | 6.3 | 6.6 | 13.1 | 13.5 | 15.6 | 16.6 |
| C | 100.0 | 85.3 | 100.0 | 37.2 | 77.4 | 19.5 | 19.2 | 28.8 |
| D | 100.0 | 96.3 | 88.1 | 57.4 | 43.7 | 16.2 | 30.5 | 5.9 |
| E | 94.4 | 86.6 | 64.6 | 90.8 | 69.4 | 92.0 | 18.6 | 50.4 |
| F | 100.0 | 99.0 | 82.9 | 89.8 | 79.2 | 93.8 | 30.1 | 32.5 |
| G | 100.0 | 95.3 | 100.0 | 98.2 | 96.7 | 93.6 | 42.5 | 27.4 |
| H | 100.0 | 100.0 | 99.2 | 95.6 | 95.7 | 89.7 | 39.8 | 36.3 |

EXAMPLE 10

Molasses (20 g) was mixed thoroughly with corn oil (1 g). To obtain water dispersible gluten particles, gluten (20 g) was mixed with a molasses-oil mixture (5 g) and allowed to dry at room temperature. The resulting products were granules that dispersed in water quickly and could be applied by spraying. About 50 ml of dispersible gluten was added to tap water (1 g), followed by the addition of wettable powdered elemental sulfur (1 g). The pH of the mixture was adjusted to 11 by the addition of a diluted KOH solution. Freshly harvested cotton leaves (9 cm in diameter) were treated with the gluten-sulfur mixture (0.7 ml). As a control, the experiment was repeated using cotton leaves treated with a suspension of elemental sulfur as above but without gluten. Both samples were first allowed to dry at room temperature, followed by rinsing with tap water (1 liter) applied over a 60 seconds period. The leaves were then dried at 75° for 1 hour and analyzed for sulfur.

Sulfur in control sample=0.9%

Sulfur in gluten sample=1.9% (corrected for S present in gluten).

The experiment was repeated using corn leaves with the following results:

Sulfur in control sample=1.2 %

Sulfur in gluten sample=2.8% (corrected for S present in gluten).

In another experiment, water dispersible gluten (1 g) was mixed with tap water (100 ml) along with WEEDONE® (2, 4-D formulation (1 g). (2,4-dichlorophonoxyacetic acid ester). The pH was adjusted to 11 as above to yield a stable emulsion of the herbicide to control broad-leaf weeds.

EXAMPLE 11

The following gluten formulations were made with the herbicide trifluralin.

(A) Gluten (12.5 g) was mixed in a blender with a 0.2% (w/v) KOH solution (250 ml). A sample of this mixture (19 g) was blended with trifluralin emulsifiable concentrate (1 g).

(B) Gluten (12.5 g) was mixed in a blender with a 0.2% (w/v) citric acid solution (250 ml). A sample of this mixture (19 g) was blended with trifluralin emulsifiable concentrate (1 g).

(C) Trifluralin emulsifiable concentrate (1 g) was mixed with water (19ml).

Samples of (A), (B) and (C) were placed as droplets onto separate glass microscope slides. Following drying at ambient temperature, the slides were rinsed with n-hexane. Trifluralin from (A) and (B) remained practically intact, but the active ingredient from (C) was completely washed out. This test revealed that the film formed with the gluten, under acidic or alkaline pH conditions, effectively encapsulated the trifluralin.

In another experiment, slides (A), (B) and (C) were dried at ambient temperature, then subjected to enhanced evaporation of the active ingredient at 60° C. for 2 hours. The trifluralin remained essentially intact in (A) and (B) but it essentially all evaporated from (C). Furthermore, the gluten film in (A) and (B) adhered to the glass and resisted wash out with water.

Additional studies were carried out with the following formulations.

(D) Trisodium phosphate (1 g) was dissolved in water (2ml), mixed thoroughly with gluten (9 g), and dried at ambient temperature to yield a fine powder with a pH of 9.8 (1% conc. in aleionized water). Part of this mixture (8 g) was blended with a melt of technical grade trifluralin (2 g) to yield a water dispersible product. 1 g was added to 100ml water and applied dropwise to glass microscope slides. A film formed upon drying that did not dislodge during the application of 1L water over a 30 second period. Retention of the characteristic yellow color of trifluralin indicated retention of the herbicide.

(E) Trisodium phosphate (TSP) (5 g) was dissolved in water (9ml) and Dextrin 200 (commercial product made by Staley, Decatur, Ill.; 5 g) and mixed with gluten (45 g) using a morter and pestel. Drying at ambient temperature produced a fine powder which passed 40 mesh. A melt of technical grade trifiuralin (2 g) was mixed with gluten-TSP-dextrin (8 g) polymeric glucose to yield a water dispirsable product.

(F) Citric acid monohydrate (0.5 g) was mixed with $CaCl_2 2H_2O$ (0.5 g), gluten (18 g) and a melt of technical grade trifluralin (2 g) to yield a water dispersible product with a pH of 3.75 (1% solid in deionized water).

EXAMPLE 12

Paraquat is a herbicide commonly used to defoliate cotton prior to harvest. Gluten (6 g) was mixed in a blender with a 0.1% (w/v) citric acid solution (600 ml) and an aqueous solution of paraquat (29% active ingredient, 10 ml). Mature cotton was sprayed in the field to run-off with this mixture.

Within hours, leaves began to curl and wither and, after 2 days, leaves were brown. Within 4 days, leaves had fallen off.

The foregoing examples demonstrate the effectiveness of a formulation of the present invention.

REFERENCES

The references listed below and all references cited herein are incorporated herein by reference to the extent that they supplement, explain, provide a background for, or teach methodology, techniques, and/or compositions employed herein.

Adamek et al., U.S. Pat. No. 3,111,416, (1963).
Arannnyi et al., U.S. Pat. No. 3,607,370 (1971). Blish, M. J., *Advances in Protein. in Chemistry*, II:337–359 (1945).
Chung, O. K., *Cereal Foods World*, 31:242–256 (1986).
Dunkle, R. L., and Shasha, B. S., *Environ. Entomol.* 17:120–126 (1988).
Hughes, P. R., and Wood, H. A., *J. Invertebr. Pathol.* 37:154–159 (1981).
Koestler, R. C., Microencapsulation by interfacial polymerization techniques—agricultural applications, pp. 117–132. In A. F. Kydonieus [ed.] Controlled release technologies: methods, theory, and applications. CRC Press, Boca Raton (1981).
Krull, L. H. and Inglett, G. E., *Cereal Science Today*, 16:232–236 (1971).
Krull, L. H. and Wall, J. S., *Canadian J. Biochem.*, 47:581–585 (1969).
Lampman, R. L. and Metcalf, R. L., *Environ. Entomol.* 17:644–648 (1988).
Lance, D. R., *J. Chem.. Ecol.* 14: 1177–1185 (1988).
Lance, D. R., and Sutter, G. R., *J. Econ. Entomol.* 83:1085–1090 (1990).
Lund, R. L., MSUSTAT Statistical Analysis Package, vers 4.1. Research and Development Institute. Bozeman, MT (1988).
Magnuson, K. M., *Cereal Foods Worhl*, 30:179–181 (1985).
McGuire et al., *J. Econ. Entomol.* 83:2207–2210 (1990).
McGuire et al., *J. Econ. Entomol.* 84:1652–1656 (1991).
McGuire, M. R. and Shasha, B. S., *J. of Econ. Entomol.* 83:1813–1817 (1990).
Meinke et al., *J. Econ. Entomol.* 82:1830–1835 (1989).
Meredith et al., *Cereal Science Today*, 9:33,54 (1964).
Metcalf, R. L. & Lampman, R. L., *J. Econ. Entomol.* 82:1830–1625 (1989).
Rosen et al., *J. Econ. Entomal.* 59:620–622 (1966).
Shasha et al., *J. Appl. Polym,. Sci.* 29:67–73 (1984).
Shasha, B. S. & M. R. McGuire. Slow release formulations of pesticides. In
D. G. Chasin & L. E. Bode, (eds), Pesticide formulations and application systems. American Society for Testing and Materials, Philadelphia (1991).
Shaw et al., *J. Econ. Entomol.* 77:1495–1499 (1984).
Shotwell, R. L., *USDA Te. ch. Bull.* 793 (1944).
Trimnell et al., *J. of Applied Polymer Science*, 27:3919–3928 (1982).
Trimnell, D. and Shasha, B. S., *J. Controlled Release* 7:263–268 (1988).
Synek, J., Formulation, development, and application of an insecticide granule, pp. 123–131. In T. M. Kaneko & N. B. Akesson [eds.] Pesticide formulations and application systems: third symposium, ASTM STP 828. American Society for Testing and Materials, Philadelphia, 1983.
Vander Hooven, D. I. B., Corncob granules and pelleted carriers— new, controlled, safer methods of handling pesticides, pp. 132–140. In T. M. Kaneko & N. B. Akesson [eds.] Pesticide formulations and application systems: third symposium, ASTM STP 828. American Society for Testing and Materials, Philadelphia, 1983.
Wall et al., *J. Polymer Sci.,* 24:147–161 (1968).
Wall, J. S. and Beckwith, A. C., *Cereal Science Today*, 14:2455 (1969).
Wall, J. S. and Huebner, F. R., *Protein Functionality in Foods* 147:110–130 (1980).
Weissling, T. J. & Meinke, L. J., *J. Econ. Entomol.* 84:601–609 (1991).
Wing, R. E. and Otey, T. H., *J. Polym.. Sci. Polym. Chem.* Ed. 21:121–140 (1983).

What is claimed is:

1. A gluten-base formation comprising gluten, a pesticidally effective amount of a pest control agent, a pH adjuster, and an aqueous solvent, said pH adjuster which is present in an amount such that the pH of the gluten-based formulation is in the range of from about 3.0 to about 5.0 or from about 9.5 to about 12.0 and wherein said gluten is solubilized and is present in a concentration of from about 0.1 grams per 100 milliliters to about 5 grams per 100 milliliters when said formulation is mixed with an aqueous solvent.

2. The formulation according to claim 1 wherein the pH is in the range of from about 9.5 to about 12.

3. The formulation of claim 2 wherein the pH is in the range of from about 10 to about 12.

4. The formulation according to claim 1 wherein said pest control agent is a bacterium, a fungus, a virus, a protozoa or a nematode.

5. The formulation according to claim 4 wherein said bacterium is *bacillus thuringiensis*.

6. The formulation according to claim 1 wherein said pest control agent is dimilin, malathion, carbaryl or 0,0-diethyl 0-[6-methyl-2-(1-methylethyl)-4-pyrimidinyl] phosphorothioate.

7. The formulation according to claim 1 wherein said pest control agent is 2,4-D, metalochlor, glyphosate, paraquat or trifluralin.

8. The gluten-based formulation of claim 1 wherein the pH is in the range of from about 3.0 to about 5.0 comprising gluten, a pesticidally effective amount of a pest control agent, and an acidifying agent, said acidifying agent which is present in an amount such that the pH is in range of from 3.0 and about 5.0.

9. The formulation according to claim 8 wherein the pH of said formulation is between about 3.0 and 3.75.

10. A process of delivering a pest control agent comprising spraying the formulation of claim 1 onto an external surface of an organism.

11. The formulation according to claim 1 wherein the concentration of gluten is from about 0.25 grams per 100 milliliters to about 1.5 grams per 100 milliliters.

* * * * *